United States Patent [19]

Magori

[11] Patent Number: 5,325,703
[45] Date of Patent: Jul. 5, 1994

[54] METHOD FOR IDENTIFYING THE CONCENTRATION OF FUELS OR GASES

[75] Inventor: Valentin Magori, Munich, Fed. Rep. of Germany

[73] Assignee: Siemens Aktiengesellschaft, Munich, Fed. Rep. of Germany

[21] Appl. No.: 950,235

[22] Filed: Sep. 24, 1992

[30] Foreign Application Priority Data

Sep. 26, 1991 [EP] European Pat. Off. ........ 91116461.4

[51] Int. Cl.$^5$ ............................................. G01N 29/02
[52] U.S. Cl. ................................. 73/23.32; 73/24.01; 73/24.04; 123/510; 123/494; 137/88; 367/13; 367/191
[58] Field of Search ............. 73/23.32, 24.01, 24.04; 367/13, 191; 137/88.9, 92; 123/510, 494

[56] References Cited

U.S. PATENT DOCUMENTS

| | | |
|---|---|---|
| 4,003,242 | 1/1977 | Houben et al. |
| 4,007,625 | 2/1977 | Houben et al. .................. 73/24.01 |
| 4,163,384 | 8/1979 | Blakemore ....................... 73/24.04 |
| 4,220,040 | 9/1980 | Noguchi et al. ................. 73/24.01 |
| 4,246,773 | 1/1981 | Haruta ............................. 73/24.01 |
| 4,424,703 | 1/1984 | Winter et al. |
| 4,630,482 | 12/1986 | Traina ............................. 73/24.01 |
| 4,656,864 | 4/1987 | Kraus et al. .................... 73/24.01 |
| 4,663,977 | 5/1987 | Vander Heyden .............. 73/24.01 |

FOREIGN PATENT DOCUMENTS

| | | |
|---|---|---|
| 2110629 | 9/1972 | Fed. Rep. of Germany . |
| 3417734 | 11/1985 | Fed. Rep. of Germany . |
| 3544786 | 6/1987 | Fed. Rep. of Germany . |
| 2592716 | 7/1987 | France ............................ 73/23.32 |
| WO87/06703 | 11/1987 | PCT Int'l Appl. . |
| 2027198 | 2/1980 | United Kingdom . |

*Primary Examiner*—Timothy M. McMahon
*Attorney, Agent, or Firm*—Hill, Steadman & Simpson

[57] ABSTRACT

The present invention discloses a method for identifying the concentration of fuels or gases in air, particularly in the intake of motor vehicle motors, with ultrasound measurement, comprising the steps of conducting an air/vapor mixture whose concentration is to be identified through an ultrasound measuring section of known length, directing ultrasound through the mixture in the measuring section, determining the speed of sound through the air/vapor mixture; and identifying the concentration of the mixture on the basis of the speed of sound through the mixture in the measuring section.

23 Claims, 2 Drawing Sheets

METHOD FOR IDENTIFYING THE CONCENTRATION OF FUELS OR GASES

BACKGROUND OF THE INVENTION

The present invention relates to a method for identifying the concentration of fuels or gases in air. More particularly, the present invention relates to a method for identifying the concentration of fuels or gases in the intake air of motor vehicle motors with ultrasound measurements. Further, the present invention relates to an apparatus for identifying the concentration of fuels or gases in air.

Motor vehicle fuel tanks have been recently equipped with activated carbon filters that bond fuel vapors. The carbon filters prevent the vapors from escaping into the atmosphere. In the regeneration of the filters, the fuel vapors bonded to the filters are transported into the intake air of the motor and are subsequently burned in the motor.

For an optimum pilot control of a given air/fuel ratio, the proportion of fuel supplied to the intake air from the activated carbon filter must be taken into consideration. A sensor for the concentration of the fuel vapor in the intake air would be expedient for this purpose. Prior proposals or attempted solutions for identifying the air/fuel ratio are based on what are referred to as chemosensors.

SUMMARY OF THE INVENTION

The present invention discloses a new method for rapidly and reliably identifying the concentration of fuels or gases in air particularly in the intake of air in motor vehicle motors, with ultrasound measurements. Further, the present invention discloses a simple and cost-beneficial apparatus for identifying the concentration of fuels or gases in air.

The identification of the concentration of fuels or gases in air is inventively achieved by evaluating the speed of sound. In an embodiment, the speed of sound is evaluated from average running times, or their reciprocals, in ultrasound air mass meters. In an embodiment, the speed of sound is evaluated from phase angles, or their reciprocals, in ultrasound air mass meters. Various fuel compositions can be estimated from a chronological curve of the measured speed of sound which derives following an impediment, such as activated carbon filters.

The present invention allows the efficiency of activated carbon filters to be monitored. Moreover, it allows the gasoline vapor concentration to be taken into consideration in metering the fuel.

DESCRIPTION OF THE PREFERRED EMBODIMENTS

The present invention discloses a unique method for identifying the fuel vapor concentration in the intake of air by measuring and evaluating the speed of sound of the air/vapor mixture.

Figure 1:
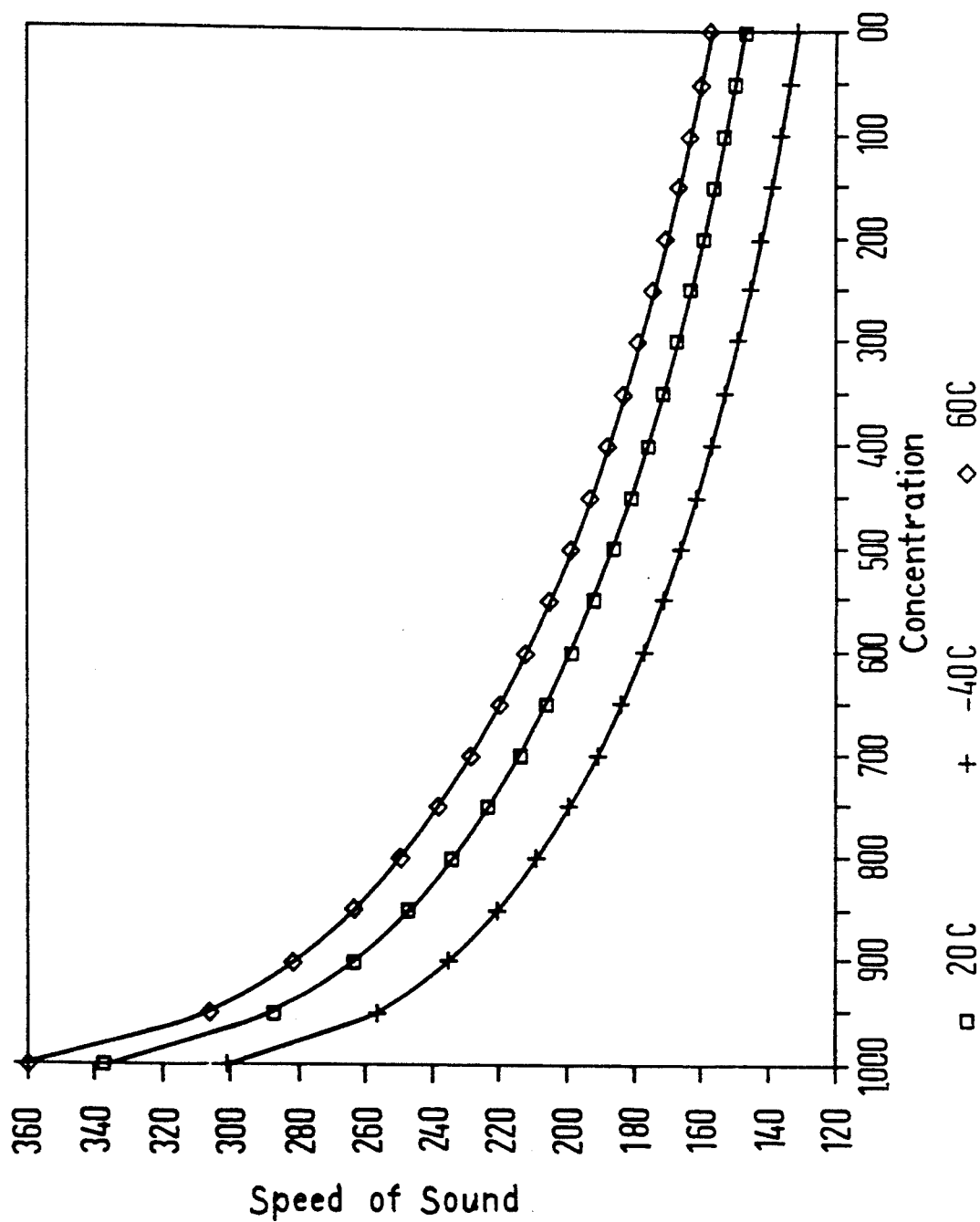
FIG. 1 is a plot diagram illustrating the speed of sound in an air/fuel mixture as a function of the vapor concentration at various temperatures.

FIG. 1 illustrates a plot diagram of the speed of sound, c, in meters per second of an air/fuel mixture as a function of the vapor concentration at different temperatures. Specifically, FIG. 1 illustrates the speed of sound, c, versus vapor concentration at three temperature (20° C.=293° K., −40° C.=233° K., 60° C.=312° K.).

Figure 2:
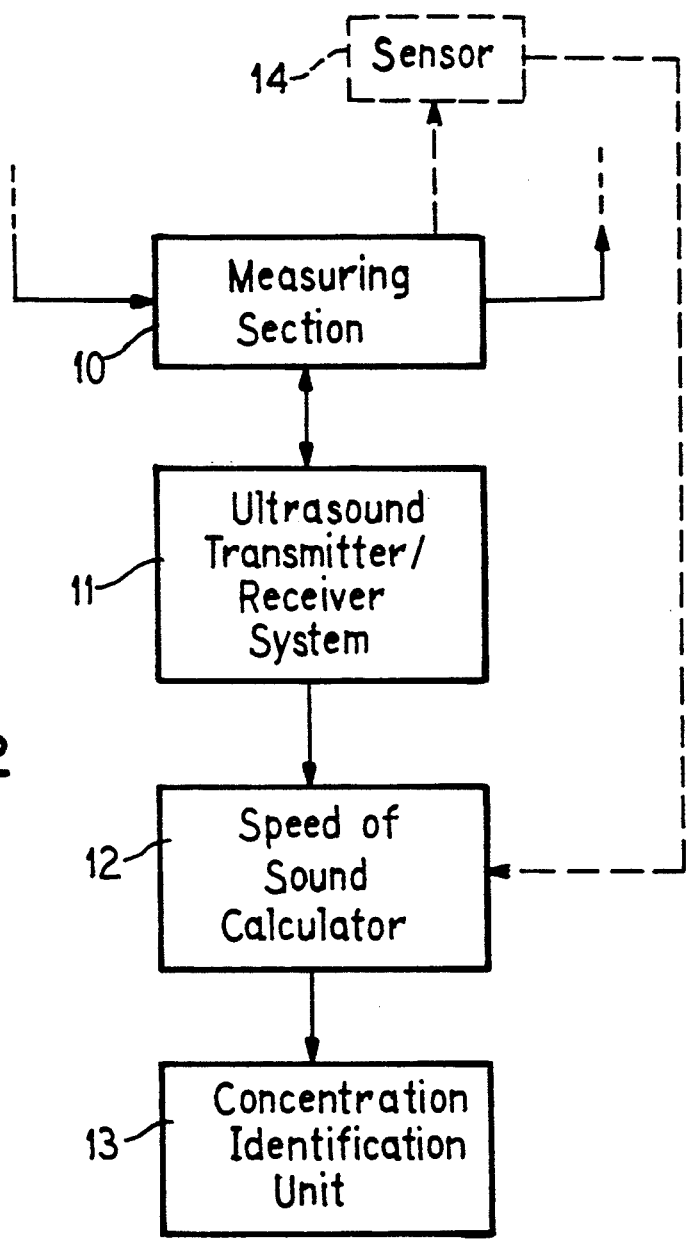
FIG. 2 is a block diagram of an apparatus for identifying the concentration of fuels or gases in air, in accordance with the principles of the present invention.

FIG. 2 illustrates an apparatus of the present invention. An ultrasound transmitter/receiver system 11 forms a measuring section 10 of known length. In an embodiment, the ultrasound transmitter/receiver system 11 comprises an ultrasound transducer for transmission and one for reception arranged at respective ends. In another embodiment, the ultrasound transmitter/receiver system 11 comprises a single transducer used for transmission and reception in chronological succession and one or more sound reflectors arranged at respective ends.

Still referring to FIG. 2, a speed of sound calculator 12 reads signals transmitted from the ultrasound transmitter/receiver system 11. The speed of sound is determined by measuring a running time at the measured section 10 of known length. The speed of sound calculator 12 may be a computer, a microprocessor, or any other instrument capable of calculating the speed of sound, such as an air mass meter.

The speed of sound is dependent on a number of parameters. It is dependent on the molecular weight and the temperature in the following manner:

$$c = \sqrt{R \cdot T \cdot X/M}$$

where R is the general gas constant, X is the ratio of the specific heats, T is the temperature in Kelvins, and M is the molecular weight. In addition, the speed of sound in gas mixtures is dependent on the mixing ratio of the constituents. With two constituents, the speed of sound is calculated from the formula:

$$c = \sqrt{\frac{RT}{x \cdot M1 + (1-x) \cdot M2} \cdot \frac{x \cdot cp1 + (1-x) \cdot cp2}{x \cdot cv1 + (1-x) \cdot cv2}}$$

where x is the mixing ratio, cp1 and cv1 are the specific heats of constituent 1, cp2 and cv2 are the specific heats of constituent 2, and M1 and M2 are the molecular weights of constituents 1 and 2 respectively.

A variety of methods are available for identifying the running time or equivalent quantities from which the speed of sound can be derived. For example, the following exemplary methods may be utilized in the present invention: 1) direct measurement of the running time or of the phase angle between transmission and reception signals; 2) measurement of the "reciprocal running time," otherwise referred to as "Sing Around" method and the derivatives thereof ("Flying Wheel," etc.); 3) measurement of the reciprocal phase angel ("Lambda Locked Loop" frequencies), with versions thereof for unambiguous identification of the absolute value of the phase angle (measurement with different orders, "Lambda Set and Lock," etc.); and 4) identification of the phase steepness dO/df of the measured section, CW sonar method.

In a preferred embodiment, the speed of sound is determined with an ultrasound air mass meter or with an ultrasound-sampled Vortex air mass meter. Following the use of the air mass meter, a chronological averaging of a plurality of acquired values can be conducted to enhance the precision of the speed of sound determination. Alternatively, a mean value calculation over a plurality of running times will also enhance the precision of the speed of sound determination.

Moreover, a number of ways exist for deriving parameters required for correcting speed influences. For instance, potentially disturbing influences of the flow rate can be theoretically derived or empirically identified and can be corrected based on the measure of the flow rate identified with the air mass meter.

Alternatively, the parameters required for correction can be derived from sensor signals. FIG. 2 illustrates an exemplary sensor 14 incorporated within the measuring section 10. Sensor 14 transmits signals to the speed of sound calculator 12 for correction of speed influences. For example, the sensor 14 can measure an inlet pipe pressure of a motor vehicle motor.

Still further, the parameters can be derived from either operating parameters of the motor vehicle motor based on empirically identified relationships or on the basis of models of the system to be considered.

Referring again to FIG. 2, the apparatus of the present invention also includes a concentration identification unit 13. The concentration identification unit 13 identifies the concentration of an air/fuel mixture based on the speed of sound through the mixture in a measuring section 10. The concentration identification unit 13 may be in the form of a graph, such as FIG. 1, or any other linear measurement display.

Although modifications and changes may be suggested by those skilled in the art, it is the intention of the inventor to embody within the patent warrented hereon all changes and modifications as reasonably and properly come within the scope of the contribution to the art.

I claim:

1. A method for identifying the concentration of fuels or gases in air comprising the steps of:
   conducting an air/fuel mixture whose concentration is to be identified through an ultrasound measuring section of known length;
   directing ultrasound through said mixture in said measuring section;
   determining the speed of sound through said air/fuel mixture; and
   identifying the concentration of said mixture on the basis of the speed of sound through said mixture in said measuring section.

2. The method of claim 1 wherein determining the speed of sound is further defined by measuring a running time between an ultrasound transmission signal and an ultrasound reception signal.

3. The method of claim 1 wherein determining the speed of sound is further defined by measuring a phase angle between an ultrasound transmission signal and an ultrasound reception signal.

4. The method of claim 1 wherein determining the speed of sound is further defined by measuring a reciprocal running time between an ultrasound transmission signal and an ultrasound reception signal.

5. The method of claim 4 wherein measuring the reciprocal running time is further defined by the use of a "Sing Around" method.

6. The method of claim 1 wherein determining the speed of sound is further defined by measuring a reciprocal phase angle between an ultrasound transmission signal and an ultrasound reception signal.

7. The method of claim 6 wherein measuring the reciprocal phase angle is further defined by the use of a "Lambda Locked Loop" method.

8. The method of claim 1 wherein determining the speed of sound is further defined by identifying the absolute value of a phase angle between an ultrasound transmission signal and an ultrasound reception signal.

9. The method of claim 1 wherein the ultrasound has a phase steepness and wherein determining the speed of sound is further defined by determining the phase steepness of the measured section.

10. The method of claim 9 wherein determining the speed of sound is further defined by the use of a CW Sonar method.

11. The method of claim 1 comprising the additional step of deriving parameters from other sensor signals required for the correction factors influencing the determination of the speed of sound.

12. The method of claim 11 wherein deriving parameters from other sensor signals is further defined by measuring an intake pipe pressure of a motor vehicle motor and generating a sensor signal required for the correction of said factors.

13. The method of claim 11 wherein said parameters are derived from operating parameters of an appertaining motor vehicle motor on the basis of empirically identified relationships.

14. The method of claim 11 wherein the parameters are derived on the basis of models of the overall system to be considered.

15. The method of claim 1 comprising the additional step of theoretically deriving disturbing influences of the flow rate of the air/vapor mixture for the purpose of correcting the speed of sound determination.

16. The method of claim 1 comprising the additional step of empirically identifying disturbing influences of the flow rate of the air/vapor mixture for the purpose of correcting the speed of sound determination.

17. The method of claim 1 comprising the additional step of enhancing the precision of the speed of sound determination.

18. The method of claim 17 wherein enhancing the speed of sound determination is further defined by a chronological averaging of a plurality of acquired values.

19. The method of claim 18 wherein enhancing the speed of sound determination is further defined by forming a mean value over a plurality of running times.

20. An apparatus for identifying the concentration of fuels or gases in air comprising:
   an ultrasound measuring section of known length;
   means for conducting an air/fuel mixture whose concentration is to be identified through said ultrasound measuring section;
   means for directing ultrasound through said mixture in said measuring section;
   means for determining the speed of sound through said mixture; and
   means for identifying the concentration of said mixture on the basis of the speed of sound through said mixture in said measuring section.

21. The apparatus of claim 20 wherein said means for directing ultrasound through said mixture comprises an ultrasound transmission transducer and an ultrasound reception transducer arranged at respective ends.

22. The apparatus of claim 20 wherein said means for directing ultrasound through said mixture comprises a transducer functioning in alternation as an ultrasound transmission transducer and an ultrasound reception transducer, and a sound reflector arranged at the respective ends.

23. The apparatus of claim 20 wherein said means for determining the speed of sound through said mixture is an ultrasound air mass meter.

* * * * *